US00PP30449P3

(12) United States Plant Patent
Klinger, Jr.

(10) Patent No.: US PP30,449 P3
(45) Date of Patent: Apr. 30, 2019

(54) ***VIBURNUM* PLANT NAMED 'BRANT01'**

(50) Latin Name: *Viburnum dentatum*
Varietal Denomination: BRANT01

(71) Applicant: Paul Klinger, Jr., Bushnell, FL (US)

(72) Inventor: Paul Klinger, Jr., Bushnell, FL (US)

(73) Assignee: Plant Development Services Inc., Loxley, AL (US)

( * ) Notice: Subject to any disclaimer, the term of this patent is extended or adjusted under 35 U.S.C. 154(b) by 0 days.

(21) Appl. No.: 15/732,042

(22) Filed: Sep. 8, 2017

(65) Prior Publication Data

US 2019/0082572 P1 Mar. 14, 2019

(51) Int. Cl.
*A01H 5/00* (2018.01)

(52) U.S. Cl.
USPC ..... Plt./226
CPC ..... *A01H 5/00* (2013.01)

(58) Field of Classification Search
USPC ..... Plt./226
CPC ..... A01H 5/02; A01H 5/00
See application file for complete search history.

(56) References Cited

PUBLICATIONS http://www.gardencentermag.com/article/pacific-plug--liner/; Mar. 27, 2017; 2 pages.*

* cited by examiner

*Primary Examiner* — Kent L Bell
(74) *Attorney, Agent, or Firm* — Cassandra Bright

(57) ABSTRACT

A new and distinct *Viburnum* cultivar named 'BRANT01' is disclosed, characterized by a compact plant habit and distinctive bronze new foliage. The new variety is a *Viburnum*, normally produced as an outdoor garden or container plant.

2 Drawing Sheets

Latin name of the genus and species: *Viburnum dentatum*.
Variety denomination: 'BRANT01'.

BACKGROUND OF THE INVENTION

The new *Viburnum* cultivar is a product of chance discovery. The inventor discovered an interesting seedling growing in a field of various *Viburnum odoratissimum* commercial varieties. The parent varieties are unknown as the seedling was found growing in a commercial field of several *Viburnum odoratissimum* varieties.

This chance seedling was first observed during 2005 in a commercial nursery in Bushnell, Fla. The inventor observed this interesting plant over several years, noting the consistently bronze foliage, and compact plant habit.

Asexual reproduction of the new cultivar 'BRANT01' by softwood cuttings was first performed during the March of 2015, at a commercial greenhouse in Bushnell, Fla. Subsequent propagation has shown that the unique features of this cultivar are stable and reproduced true to type in two successive generations.

SUMMARY OF THE INVENTION

The cultivar 'BRANT01' has not been observed under all possible environmental conditions. The phenotype may vary somewhat with variations in environment such as temperature, day length, and light intensity, without, however, any variance in genotype.

The following traits have been repeatedly observed and are determined to be the unique characteristics of 'BRANT01' These characteristics in combination distinguish 'BRANT01' as a new and distinct *Viburnum* cultivar:

1. Bronze new growth.
2. Glossy foliage.
3. Compact plant form.

PARENT COMPARISON

Parent varieties are unknown.

COMMERCIAL COMPARISON

Plants of the new cultivar 'BRANT01' can be compared to an unpatented, unnamed commercial *Viburnum odoratissimum* sold in the trade. Plants are similar in most horticultural characteristics; however 'BRANT01' differs in the following:

1. The new variety has bronze new growth, the *Viburnum odoratissimum* found in the trade has green foliage.
2. Plants of the new variety are more compact in growth.

Plants of the new cultivar 'BRANT01' can be compared to the commercial variety *Viburnum odoratissimum* 'COMPACT01' U.S. Plant patent application Ser. No. 15/731,183, currently allowed for US Plant Patent. Plants are similar in most horticultural characteristics, however 'BRANT01' differs in the following:

1. The new variety has bronze new growth, *Viburnum odoratissimum* 'Compact01' has green foliage.

BRIEF DESCRIPTION OF THE PHOTOGRAPHS

Figure 1:
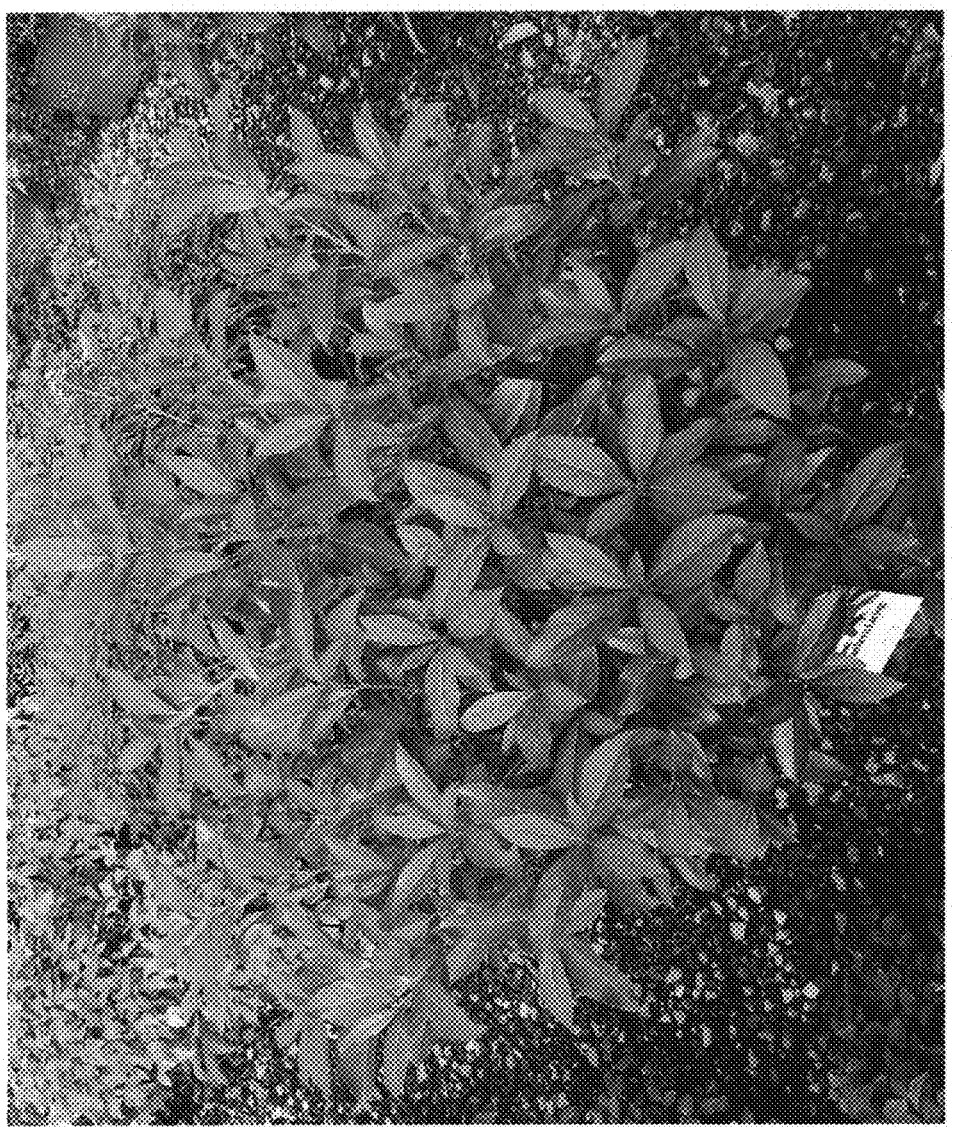

The accompanying photograph in FIG. 1 illustrates in full color a typical plant of 'BRANT01' grown outdoors in a 2 gallon nursery pot, in Loxley, Ala. during Spring.

Figure 2:
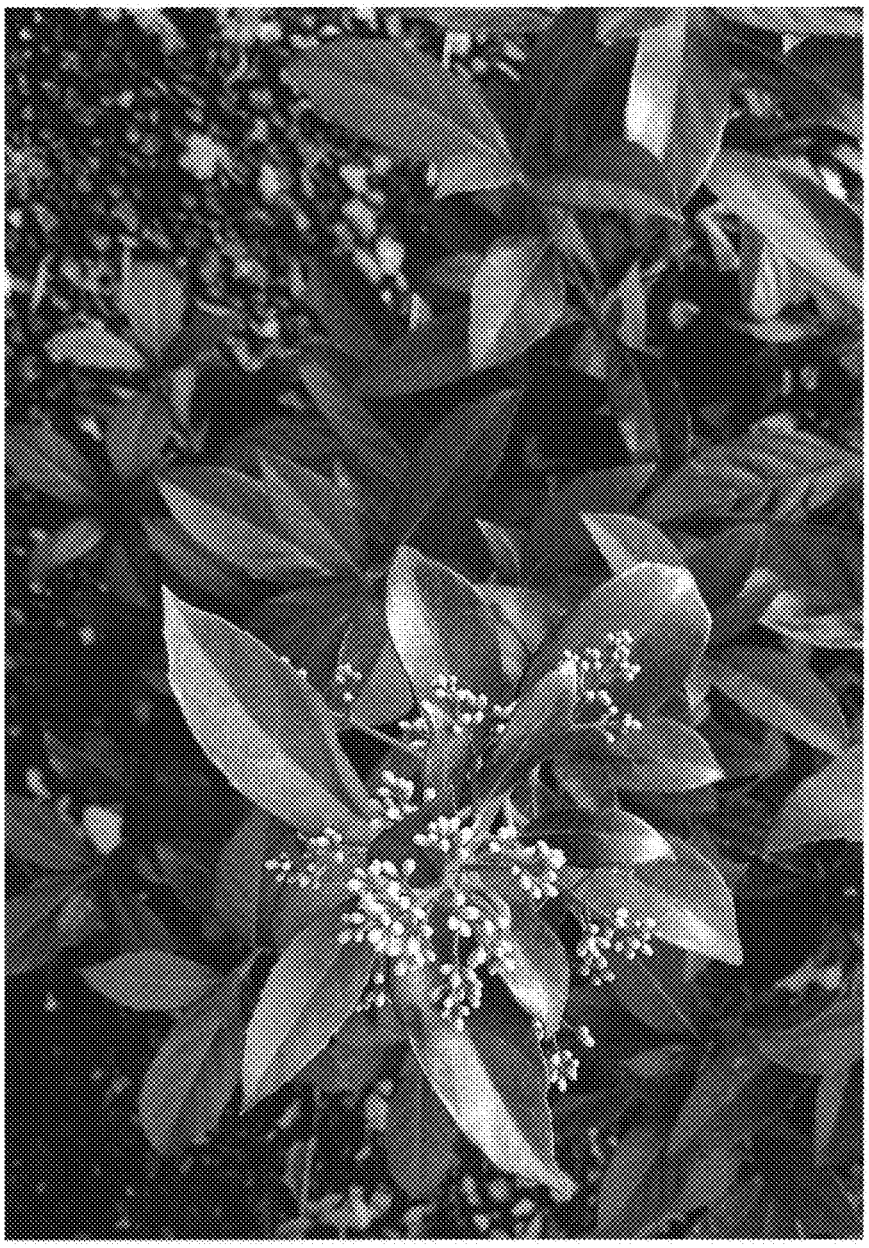

FIG. 2 illustrates in full color a typical inflorescence and new foliage of 'BRANT01'. Age of the plant photographed is approximately 2 years.

The photographs were taken using conventional techniques and although colors may appear different from actual colors due to light reflectance it is as accurate as possible by conventional photographic techniques.

DETAILED BOTANICAL DESCRIPTION

In the following description, color references are made to The Royal Horticultural Society Colour Chart 2007 except where general terms of ordinary dictionary significance are used. The following observations and measurements describe 'BRANT01' plants grown outdoors at a commercial nursery in Loxley, Ala. under natural lighting. Measurements were taken during Spring of 2015. The plants described were 2 years old in 1 gallon containers. The growing temperature ranged from 5° C. to 27° C. Measurements and numerical values represent averages of typical plant types.

Botanical classification: *Viburnum odoratissimum* 'BRANT01'.

PROPAGATION

Time to initiate roots: About 30 days at approximately 24° C.

Root description: Dense density freely branching. Root thickness from thick to thin. White to brown in color, not effectively measured with a color chart.

Time to produce a rooted young plant: About 120 days at 24° C.

PLANT

Plant type: Evergreen perennial shrub.

Age of plant described: Approximately 2 years old.

Pot size of plant described: 1 gallon pot.

Overall plant shape: Outward "V" shape.

Height: 30 cm.

Plant spread: 35 cm.

Growth rate: Moderate to rapid.

Plant vigor: Good.

Branching characteristics: Opposite, basal branching. Pinching required.

Length of primary lateral branches: 20 cm.

Diameter of lateral branches: 1 cm.

Quantity of lateral branches: About 5 lateral branches per main branch.

Stem:

- *Stem appearance*.—Round.
- *Stem strength*.—Strong.
- *Stem color*.—Newest growth near RHS Yellow-Green 144B. Mid season growth near RHS Yellow-Green 144A, densely covered in lenticels colored near Greyed-Orange 176B. Lenticels round, less than 1 mm. Oldest growth develops bark, colored near greyed-Orange 177C.
- *Pubescence*.—Slight rough pubescence on newest growth.
- *Aspect*.—Upright 45°.

Internode length: Average 3 cm.

FOLIAGE

Leaf:

- *Arrangement*.—Opposite.
- *Leaf shape*.—Elliptic.
- *Average length*.—Average range 6 to 9 cm.
- *Average width*.—2.5 cm.
- *Apex*.—Acute.
- *Base*.—Attenuate.
- *Margin*.—Infrequent shallow dentations, more frequent towards apex.
- *Texture of top surface*.—Glabrous.
- *Texture of bottom surface*.—Glabrous.
- *Appearance of top surface*.—Glossy.
- *Appearance of bottom surface*.—Matte with shiny veins.
- *Color*.—New foliage upper side: Near RHS Greyed-Purple 184B. New foliage under side: Near Greyed-Red 178B, with a slight sheen Yellow-Green N144A. Young foliage upper side: Greyed-Orange 176A, with slight flushing near veins N144B. Young foliage under side: Greyed-Orange 177C, with flushing near veins N144B. Mature foliage upper side: Near RHS Green 137A. Mature foliage under side: Near RHS Green 138B.
- *Venation*.—Pattern: Pinnate. Color upper side: Near RHS Yellow-Green N144B. Color under side: Near RHS Yellow-Green N144B.
- *Petiole*.—Average Length: 1.0 cm. Diameter: 3 mm. Petiole color lower side: Near RHS Yellow-green 144B. Petiole Texture upper side: Glabrous. Petiole Texture lower side: Glabrous.

FLOWER

Natural flowering season: Late Spring to early Summer.

Inflorescence type and habit: Terminal umbel.

Flower longevity on plant: 2 to 3 weeks.

Quantity of flowers per inflorescence: Approximately 50 to 200.

Inflorescence size:

- *Width*.—Approximately 9 to 15 cm.
- *Height*.—Approximately 8 to 11 cm.

Individual flowers:

- *Flower form*.—Rotate, single whorl.
- *Flower aspect*.—Upward facing.
- *Size*.—Diameter: Approximately 4 to 8 mm. Depth: Approximately 4 mm. Flower tube diameter: 1 mm. Flower tube length: 2 mm.

Flower other characteristics:

- *Persistence*.—Self cleaning.
- *Fragrance*.—Sweet, moderate.

Petal:

- *Petal arrangement*.—Single whorl.
- *Number of petals per flower*.—5.
- *Petal shape*.—Orbicular to ovate.
- *Petal base*.—Obtuse.
- *Margin*.—Entire.
- *Tip shape*.—Obtuse.
- *Length*.—4 mm.
- *Width*.—3 mm.
- *Texture*.—Upper: Smooth, silky. Lower: Smooth, silky. Tube: Smooth.

Petal color:
*When opening*.—Upper surface: Near RHS Orange-White 159B. Lower surface: Near RHS Orange-White 159B.
*Fully opened*.—Upper surface: Near RHS White 155B. Lower surface: Near RHS White 155B. Veins upper and lower: Near RHS White 155B.
Bud:
*Shape*.—Obovate.
*Length*.—Approximately 4 mm.
*Diameter*.—Approximately 3 mm.
*Color*.—Near RHS Yellow-Green 149D.
Sepals:
*Arrangement*.—Rotate, fused at base.
*Quantity*.—5.
*Shape*.—Individual sepals, narrow deltate.
*Base*.—Fused.
*Margin*.—Entire.
*Tip shape*.—Acute.
*Length*.—3 mm.
*Width*.—2 mm.
*Texture*.—Inner: Glabrous. Outer: Glabrous.
*Color*.—Inner: Green 137D. Outer: Green 138A.
Peduncle:
*Length*.—Average range 3 to 7 cm.
*Diameter*.—4 mm.
*Color*.—Near RHS Greyed-Red 181C.
*Orientation*.—Straight, approximately 70 to 90° from branch.
*Strength*.—Good.
*Texture*.—Slightly rough.
Pedicel:
*Length*.—5 mm.
*Diameter*.—1 mm.
*Color*.—Near RHS Greyed-Red 181D.
*Strength*.—Good.
*Texture*.—Glabrous.

REPRODUCTIVE ORGANS

Stamens:
*Number*.—4 to 5, misshapen, sometimes fused together.
*Filament length*.—2 mm.
*Filament color*.—Near RHS Yellow-White 158D.
Anthers:
*Shape*.—Club-like, misshapen.
*Length*.—1 mm.
*Color*.—Near RHS Yellow-White 158A.
*Pollen*.—Pollen production not observed.
Pistil:
*Number*.—1.
*Length*.—3 mm.
*Style*.—Length: 2 mm. Color: Near RHS Green 143C.
*Stigma*.—Color: Near RHS Green 143C.

OTHER CHARACTERISTICS

Seeds and fruits: Not observed to date.
Disease/pest resistance: Neither resistance nor susceptibility to normal diseases and pests of *Viburnum* have been observed.
Temperature tolerance: The new variety grows in USDA zones 8 through 11.
What is claimed is:
1. A new and distinct cultivar of *Viburnum* plant named 'BRANT01' as herein illustrated and described.

* * * * *